United States Patent [19]

Michelson

[11] Patent Number: 5,015,247

[45] Date of Patent: May 14, 1991

[54] THREADED SPINAL IMPLANT

[76] Inventor: Gary K. Michelson, 438 Sherman Canal, Venice, Calif. 90291

[21] Appl. No.: 205,935

[22] Filed: Jun. 13, 1988

[51] Int. Cl.$^5$ .................... A61F 5/04; A61F 2/44
[52] U.S. Cl. .................................. 606/61; 606/72; 623/17
[58] Field of Search ....... 128/92 ZW, 92 YQ, 92 YG, 128/92 YM, 92 YJ, 92 YC, 92 YE; 623/16, 17, 18, 19, 20; 606/72, 73, 76, 77, 78, 99, 95, 60, 65, 61

[56] References Cited

U.S. PATENT DOCUMENTS

| | | | |
|---|---|---|---|
| 2,543,780 | 3/1951 | Hipps | 128/92 YJ |
| 3,128,768 | 4/1964 | Geistauts | 128/92 V |
| 3,426,364 | 2/1969 | Lumb | 128/92 YM |
| 3,848,601 | 11/1974 | Ma | 623/17 |
| 4,124,026 | 11/1978 | Berner | 128/92 V |
| 4,177,524 | 12/1979 | Grell | 128/92 YF |
| 4,259,072 | 3/1981 | Hirabayashi | 128/92 YF |
| 4,289,123 | 9/1981 | Dunn | 128/92 YC |
| 4,309,777 | 1/1982 | Patil | 623/17 |
| 4,328,593 | 5/1982 | Sutter | 6232/17 |
| 4,349,921 | 9/1982 | Kuntz | 623/17 |
| 4,401,112 | 8/1983 | Rezaian | 128/92 YM |
| 4,501,269 | 2/1985 | Bagby | 128/92 YJ |
| 4,553,273 | 11/1985 | Wu | 128/92 YM |
| 4,599,086 | 7/1986 | Doty | 128/92 YM |
| 4,636,217 | 1/1987 | Ogilvie | 623/17 |
| 4,653,486 | 3/1987 | Coker | 128/92 YC |
| 4,714,469 | 12/1987 | Kenna | 128/92 YM |
| 4,736,738 | 4/1988 | Lipovsek | 128/92 YJ |
| 4,743,256 | 5/1988 | Brantigan | 623/17 |
| 4,743,260 | 5/1988 | Burton | 128/92 YM |
| 4,790,303 | 12/1988 | Steffee | 128/92 YJ |

FOREIGN PATENT DOCUMENTS 3132520 6/1982 Fed. Rep. of Germany ........ 128/92 YM

Primary Examiner—Robert A. Hafer
Assistant Examiner—Michael Brown
Attorney, Agent, or Firm—Lewis Anten

[57] ABSTRACT

An artificial spinal implant is disclosed which when placed between two adjacent vertebrae directly participates and is incorporated in the ensuing fusion. Instrumentation and procedure is also disclosed.

9 Claims, 6 Drawing Sheets

THREADED SPINAL IMPLANT

BACKGROUND

The present invention relates to an artificial fusion implant to be placed into the intervertebral space left after the removal of a damaged spinal disc.

The purpose of the present invention is to provide an implant to be placed within the intervertebral disc space and provide for the permanent elimination of all motion at that location. To do so, the device is space occupying within the disc space, rigid, self-stabilizing to resist dislodgement, stabilizing to the adjacent spinal vertebrae to eliminate local motion, and able to intrinsically participate in a vertebral to vertebra bony fusion so as to assure the permanency of the result.

At present, following the removal of a damaged disc, either bone or nothing is placed into the space left. Placing nothing in the space allows the space to collapse which may result in damage to the nerves; or the space may fill with scar tissue and eventually lead to a reherniation. The use of bone is less than optimal in that the bone obtained from the patient requires additional surgery and is of limited availability in its most useful form, and if obtained elsewhere, lacks living bone cells, carries a significant risk of infection, and is also limited in supply as it is usually obtained from accident victims. Furthermore, regardless of the source of the bone, it is only marginal structurally and lacks a means to either stabilize itself against dislodgement, or to stabilize the adjacent vertebrae.

A review of related prior art will demonstrate the novelty of the present invention.

There have been an extensive number of attempts to develop an acceptable disc prothesis (an artificial disc). Such devices by design would be used to replace a damaged disc and seek to restore the height of the interspace and to restore the normal motion of that spinal joint. No such device has been found that is medically acceptable. This group of prosthetic or artificial disc replacements, seeking to preserve spinal motion and so are different from the present invention, would include:

U.S. Pat. No. 3,867,728 STUBSTAD—describing a flexible disc implant.

U.S. Pat. No. 4,349,921 KUNTZ—describing a flexible disc replacement with file like surface projections to discourage device dislocation.

U.S. Pat. No. 4,309,777 PATIL—describing a motion preserving implant with spiked outer surfaces to resist dislocation and containing a series of springs to urge the vertebrae away from each other.

U.S. Pat. No. 3,875,595 FRONING—describing a motion preserving bladder like disc replacement with two opposed stud-like projections to resist dislocation.

U.S. Pat. No. 2,372,622 (Fassio)—describing a motion preserving implant comprising complimentary opposed convex and concave surfaces.

In summary then, these devices resemble the present invention only in that they are placed within the intervertebral space following the removal of a damaged disc. In that they seek to preserve spinal motion, they are diametrically different from the present invention which seeks to permanently eliminate all motion at that spinal segment.

A second related area of prior art includes those devices utilized to replace essentially wholly removed vertebra. Such removal is generally necessitated by extensive vertebral fractures, or tumors, and is not associated with the treatment of disc disease. While the present invention is to be placed within the disc space, these other vertebral devices cannot be placed within the disc space as at least one vertebra has already been removed such that there no longer remains a "disc space." Furthermore, these devices are limited in that they seek to perform as temporary structural members mechanically replacing the removed vertebra (not a removed disc), and do not intrinsically participate in supplying osteogenic material to achieve cross vertebra bony fusion. Therefore, again unlike the present invention which provides for a source of osteogenesis, use of this group of devices must be accompanied by a further surgery consisting of a bone fusion procedure utilizing conventional technique. This group consisting of vertebral struts rather than disc replacements would include the following:

U.S. Pat. No. 4,553,273 WU—describing a turnbuckle like vertebral strut.

U.S. Pat. No. 4,401,112 REZAIAN—describing a turnbuckle like vertebral strut with the addition of a long stabilizing staple that spans the missing vertebral body.

U.S. Pat. No. 4,554,914 KAPP—describing a large distractible spike that elongates with a screw mechanism to span the gap left by the removal of a entire vertebra and to serve as an anchor for acrylic cement which is then used to replace the missing bone (vertebra).

U.S. Pat. No. 4,636,217 OGILVIE—describing a vertebral strut mechanism that can be implanted after at least one vertebra has been removed and which device consists of a mechanism for causing the engagement of screws into the vertebra above and the vertebra below the one removed.

In summary then, this group of devices differs from the present invention in that they are vertebral replacements struts, do not intrinsically participate in the bony fusion, can only be inserted in the limited circumstances where an entire vertebra has been removed from the anterior approach, and are not designed for, or intended to be used for the treatment of disc disease.

A third area of prior art related to the present invention includes all devices designed to be applied to one of the surfaces of the spine. Such devices include all types of plates, struts, and rods which are attached by hooks, wires and screws. These devices differ significantly from the present invention in that they are not inserted within the disc space, and furthermore do not intrinsically participate in supplying osteogenic material for the fusion.

Therefore, with these devices where permanent spinal immobilization is desired an additional surgery consisting of a spinal fusion performed by conventional means or the use of supplemental methylmethacrylate cement is required. Such devices applied to the spine, but not within the disc space, would include the following:

U.S. Pat. No. 4,604,995 STEPHENS—describing a "U" shaped metal rod attached to the posterior elements of the spine with wires to stabilize the spine over a large number of segments.

U.S. Pat. No. 2,677,369 KNOWLES—describing a metal column device to be placed posteriorly along the lumbar spine to be held in position by its shape alone and to block pressure across the posterior portions of the spinal column by locking the spine in full flexion thereby shifting the maximum weight back onto the patient's own disc.

Other devices are simply variations on the use of rods (e.g. Harrington Luque, Cotrel-Dubosset, Zielke), wires or cables (Dwyer), plates and screws (Steffee), or struts (Dunn, Knowles).

In summary, none of these devices are designed or can be used within the disc space, do not replace a damaged disc, and do not intrinsically participate in the generation of a bony fusion.

Another area of related prior art to be considered is that of devices designed to be placed within the vertebral interspace following the removal of a damaged disc, and seeking to eliminate further motion at that location.

Such a device is contained in U.S. Pat. No. 4,501,269 BAGBY—describing an implantable device and limited instrumentation. The method employed is as follows: a hole is bored transversely across the joint and then a hollow metal basket of larger diameter than the hole is then pounded into the hole and then filled with the bone debris generated by the drilling.

While the present invention (device, instrumentation, and method) may appear to bear some superficial resemblance to the BAGBY invention, it is minimal, while the differences are many fold and highly significant. These differences include the following:

1. Safety—The present invention provides for a system of completely guarded instrumentation so that all contiguous vital structures (e.g. large blood vessels, neural structures) are absolutely protected. Said instrumentation also makes overpenetration by the drill impossible. Such overpenetration in the cervical spine, for example, would result in the total paralysis or death of the patient. In the thoracic spine, the result would be complete paraplegia. In the lumbar spine, the result would be paraplegia or a life-threatening perforation of the aorta, vena cava, or iliac vessels. The present invention is atraumatically screwed into place while the BAGBY device, in contradistinction, is pounded into position. BAGBY describes that the implant is significantly larger in size than the hole drilled and must be pounded in. This is extremely dangerous and the pounding occurs directly over the spinal cord which is precariously vulnerable to percussive injury. Furthermore, while it is possible, for example in the lumbar spine, to insert the present invention away from the spinal cord and nerves, the BAGBY device must always be pounded directly towards the spinal cord.

Furthermore, since the BAGBY device is pounded into a smooth hole under great resistance, and lacking any specific design features to secure it, the device is highly susceptible to forceful ejection which would result in great danger to the patient and a clinical failure. The present invention, in contradistinction, is securely screwed into place, and possesses highly specialized locking threads to make accidental dislodgement impossible. Because of the proximity of the spinal cord, spinal nerves, and blood vessels, any implant dislodgement as might occur with the BAGBY device might have catastrophic consequences.

2. Broad applicability—The BAGBY device can only be inserted from the front of the vertebral column, however, the present invention can be utilized in the cervical, thoracic, and lumbar spine, and can be inserted from behind (posteriorly) in the lumbar spine. This is of great importance in that the purpose of these devices is in the treatment of disc disease and probably greater than 99 percent of all lumbar operations for the treatment of disc disease are performed from behind where the present invention can easily be utilized, but the BAGBY device, as per his description, cannot.

3. Disc removal—The BAGBY invention requires the complete removal of the disc prior to the drilling step, whereas the present invention eliminates the laborious separate process of disc removal and efficiently removes the disc and prepares the vertebral end plates in a single step.

4. Time required—The present invention saves time over the BAGBY invention in that time is not wasted laboring to remove the disc prior to initiating the fusion. Also, since with the present invention the procedure is performed through a system of guarded instrumentation, time is not wasted constantly placing and replacing various soft tissue retractors throughout the procedure.

5. Implant stability—Dislodgement of the implant would be a major source of device failure (an unsuccessful clinical result), and might result in patient paralysis or even death. As discussed, the BAGBY device lacks any specific means of achieving stability and since it is pounded in against resistance to achieve vertebral distraction, it is susceptible to forceful dislodgement by the tendency of the two distracted vertebra, to return to their original positions squeezing out the device. The present invention however is screwed into place. As there is no unscrewing force present between the vertebra and compression alone cannot dislodge the implant, the implant is inherently stable by its design. Furthermore, the threads of the present invention are highly specialized in that they are periodically interrupted such that the tail ends of each of the tabs so formed are blunted and twisted so as to resist accidental unscrewing. The removal of an implant with such "locking threads" requires the use of a special extractor included within the instrumentation. The stability of the present invention is still further enhanced, again in contradistinction to the BAGBY device, by the presence of a "bone ingrowth" surface texturing, which both increases the friction of the fit and allows for the direct growth of the vertebral bone into the casing of the implant itself.

6. Spinal stability—The present invention is not only self-stabilizing, it also provides stability to the adjacent vertebra in at least three way that the BAGBY device cannot. First, the BAGBY device is placed transversely across the joint in the center, leaving both vertebra free to rock back and forth over this round barrel shaped axis, much like a board over a barrel, being used for a seesaw.

Secondly, as the BAGBY device lacks any specific design features to resist sliding, it may actually behave as a third body allowing the translation of the vertebra relative to the device and to each other.

Thirdly, any device can only provide stability if it remains properly seated. The present invention is inherently stable, and therefore assures that it will stabilize the adjacent vertebra; rather than, as with the BAGBY device, where the instability of the spine to be treated may instead cause a dislocation of the implant, with further loss of spinal stability.

7. The collapse of the interspace—While both the present invention and the BAGBY device can be fabricated to withstand the compression forces within the interspace, the interspace may nevertheless collapse under the superincumbent body weight as the implant settles into the vertebral bone. This is related to the load per unit area. Again the present invention is superior to the BAGBY device in at least four ways. First, the present invention offers considerably greater surface area to distribute the load. Secondly, while the BAGBY device is placed centrally, the present device is placed bilaterally where the bone tends to be more cortical and much stronger out towards the rim. Thirdly, the present invention supports the load achieving an "I" beam effect, whereas the BAGBY implant does not. Fourthly, it is not pressure alone that causes the collapse of the bone adjacent to the implant, but also bony erosion that is caused by the motion under pressure of the implant against the bone. As discussed in item #6 above, the present invention alone is highly resistant to such motion, again diminishing the likelihood of erosion and interspace collapse.

8. Bone ingrowth surface texturing—The present invention has a surface treatment of known and conventional technology to induce the growth of bone from the vertebra directly into the casing material of the implant itself. Th BAGBY device has no similar feature.

9. Fusion mass—The BAGBY invention calls for removing the disc and then drilling a hole between the adjacent vertebra. The bony debris so generated is then put into the device. The present invention takes a core of pure bone producing marrow from the iliac crest, and then by use of a special press forcibly injects the device with an extremely dense compressed core of that osteogenic material until the material itself virtually extrudes from every cell of the implant.

10. The probability of achieving fusion—The fusion rate within the spine is known to be related directly to the amount of exposed vascular bone bed area, the quality and quantity of the fusion mass available, and the extent of the stabilization obtained with all other factors being hold constant. It would then be anticipated, that the fusion rate would be superior with the present invention as compared to the BAGBY device, because of optimal implant stability (#5), optimal spinal stability (#6), bone ingrowth surface treatment (#8), superior fusion mass (#9), and the greater exposed vertebral bony surface area (#7).

The last area of prior art possibly related to the present invention and therefore, to be considered related to "BONY INGROWTH", and patents either describe methods of producing materials and or materials or devices to achieve the same. Such patents would include:

U.S. Pat. No. 4,636,526 (DORMAN), U.S. Pat. No. 4,634,720 (DORMAN), U.S. Pat. No. 4,542,539 (ROWE), U.S. Pat. No. 4,405,319 (COSENTINO), U.S. Pat. No. 4,439,152 (SMALL), U.S. Pat. No. 4,168,326 (BROEMER), U.S. Pat. No. 4,535,485 (ASHMAN), U.S. Pat. No. 3,987,499 (SCHARBACH), U.S. Pat. No. 3,605,123 (HAHN), U.S. Pat. No. 4,655,777 (DUNN), U.S. Pat. No. 4,645,503 (LIN), U.S. Pat. No. 4,547,390 (ASHMAN), U.S. Pat. No. 4,608,052 (VAN KAMPEN), U.S. Pat. No. 4,698,375 (DORMAN), U.S. Pat. No. 4,661,536 (DORMAN), U.S. Pat. No. 3,952,334 (BOKROS), U.S. Pat. No. 3,905,047 (LONG), U.S. Pat. No. 4,693,721 (DUCHEYNE), U.S. Pat. No. 4,070,514 (ENTHERLY).

However, while the present invention would utilize bone ingrowth technology, it would do so with conventional technology.

In summary t hen, the present invention, instrumentation, and method, alone provides for a one stage discectomy, fusion, and interbody internal spinal fixation; that being performed more quickly, with greater safety, and more affectively, for all of the aforementioned reasons than is possible with any other known art.

BRIEF SUMMARY OF THE INVENTION

The present invention comprises a series of artificial implants, the purpose of which is to participate in, and directly cause bone fusion across an intervertebral space following the excision of a damaged disc. Such implants are structurally load bearing devices, stronger than bone, capable of withstanding the substantial forces generated within the spinal interspace. Such devices have a plurality of macro sized cells and openings, which can be loaded with fusion promoting materials, such as autogenous bone, for the purpose of materially influencing the adjacent vertebra to form a bony bond to the implants and to each other. The implant casing may be surface textured or otherwise treated by any of a number of known technologies to achieve a "bone ingrowth surface" to further enhance the stability of the implant and to expedite the fusion.

Further, said devices are so configured and designed so as to promote their own stability within the vertebral interspace and to resist being dislodged, and furthermore, to stabilize the adjacent spinal segments.

The apparatus for preparing the vertebra for insertion of the implant is also disclosed, such instrumentation and method allowing for the rapid and safe removal of the disc, preparation of the vertebra, performance of the fusion, and internal stabilization of the spinal segment.

DISCUSSION OF THE INSTRUMENTATION

The concept of performing various aspects of this surgery are not entirely new. Drills are frequently placed through hollow, tubular guards to protect the adjacent soft tissues. A set of instruments developed by Ralph Cloward utilizes such a tubular drill guard on a larger scale, for the purpose of drilling into the cervical spine. However, this inventor is unaware of any set of instruments, system, or procedure designed to allow the entire surgical procedure beyond the initial exposure, to be performed blindly and with complete safety through a fixed sheath apparatus. Specific design features which combine to make this uniquely possible are as follows:

1. The availability of the specific implant.

2. The end of all the penetrating instrumentation is blunt faced.

3. All of the instruments have been stopped out at a predetermined depth to avoid overpenetration.

4. The design of the external sheath conforms to the spacial limitations of the specific surgical site.

5. The design and use of a second or inner sheath allows for the difference in size between the inside diameter of the outer sheath, and the outside diameter of the drill itself. This difference being necessary to accommodate the sum of the distraction to be produced, and the depth of the circumferential threading present on the implant.

6. A specially designed drill bit with a central shaft recess allows for the safe collection of the drilling products, which can then be removed without disturbing the outer sheath by removing the drill bit and inner sheath as a single unit.

7. A specially designed trephine for removing a oore of bone slightly smaller in diameter than the internal diameter of the implant cavity itself, however of a greater length.

8. A specially designed press for forcefully compressing and injecting the long core of autogenous bone into the implant such that it extrudes through the implant itself.

9. A specially designed driver extractor, which attaches to the implant and allows the implant to be either inserted or removed without itself dissociating from the implant except by the deliberate disengagement of the operator.

OBJECTS OF THE PRESENT INVENTION

It is an object of the present invention to provide an improved method of performing a discectomy, a fusion, and an internal stabilization of the spine, and specifically, all three of the above simultaneously and as a single procedure.

It is another object of the present invention to provide an improved method of performing a discectomy, a fusion, and an internal stabilization of the spine, which is both quicker and safer than is possible by previous methods.

It is another object of the present invention to provide an improved method of performing a discectomy, a fusion, and an internal stabilization of the spine, to provide for improved surgical spinal implants.

It is another object of the present invention to provide an improved method of performing a discectomy, a fusion, and an internal stabilization of the spine, which provides for an improved system of surgical instrumentation to facilitate the performance of the combined discectomy, fusion, and internal spinal stabilization.

These and other objects of the present invention will be apparent from review of the following specifications and the accompanying drawings.

BRIEF DESCRIPTION OF THE DRAWINGS

FIG. 1 is a perspective view of the driver and sheath and its orientation to a vertebral structure.

DETAILED DESCRIPTION OF THE DRAWINGS

Figure 1A:
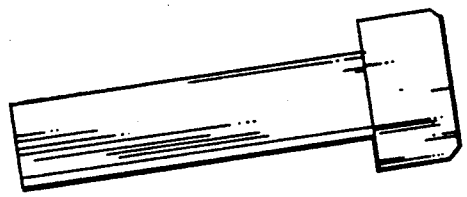
FIG. 1A is a perspective view of the driver member for the outer sheath.
Figure 1:
FIG. 1 is a partial view of the vertebra structure with the driver and outer sheath assembly of the present invention.
Figure 1:
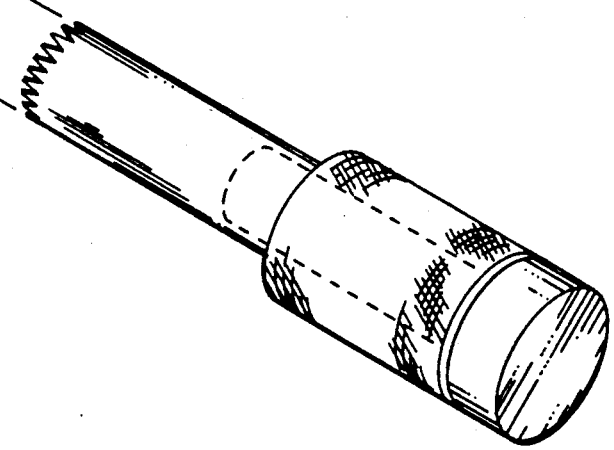

Referring to FIG. 1 a vertebra structure comprising two vertebra V and a disc D between the two vertebra, is shown. A hollow tubular drill sleeve 10 has teeth 12 at its lower end. The sleeve 10 has an enlarged diameter upper portion 14.

A driver 16, shown in FIG. 1A, consists of a solid tubular member 18 and an increased diameter head 20. The external diameter of the solid tubular member 18 is slightly smaller than the inside diameter of the hollow tubular drill sleeve 10 and has a length that is substantially shorter tha the overall length of the hollow tubular drill sleeve 10.

The drill sleeve 10 is made of metal in order to be driven into the vertebra V and be held in place by the teeth 12 of the drill sleeve 10.

Figure 2:
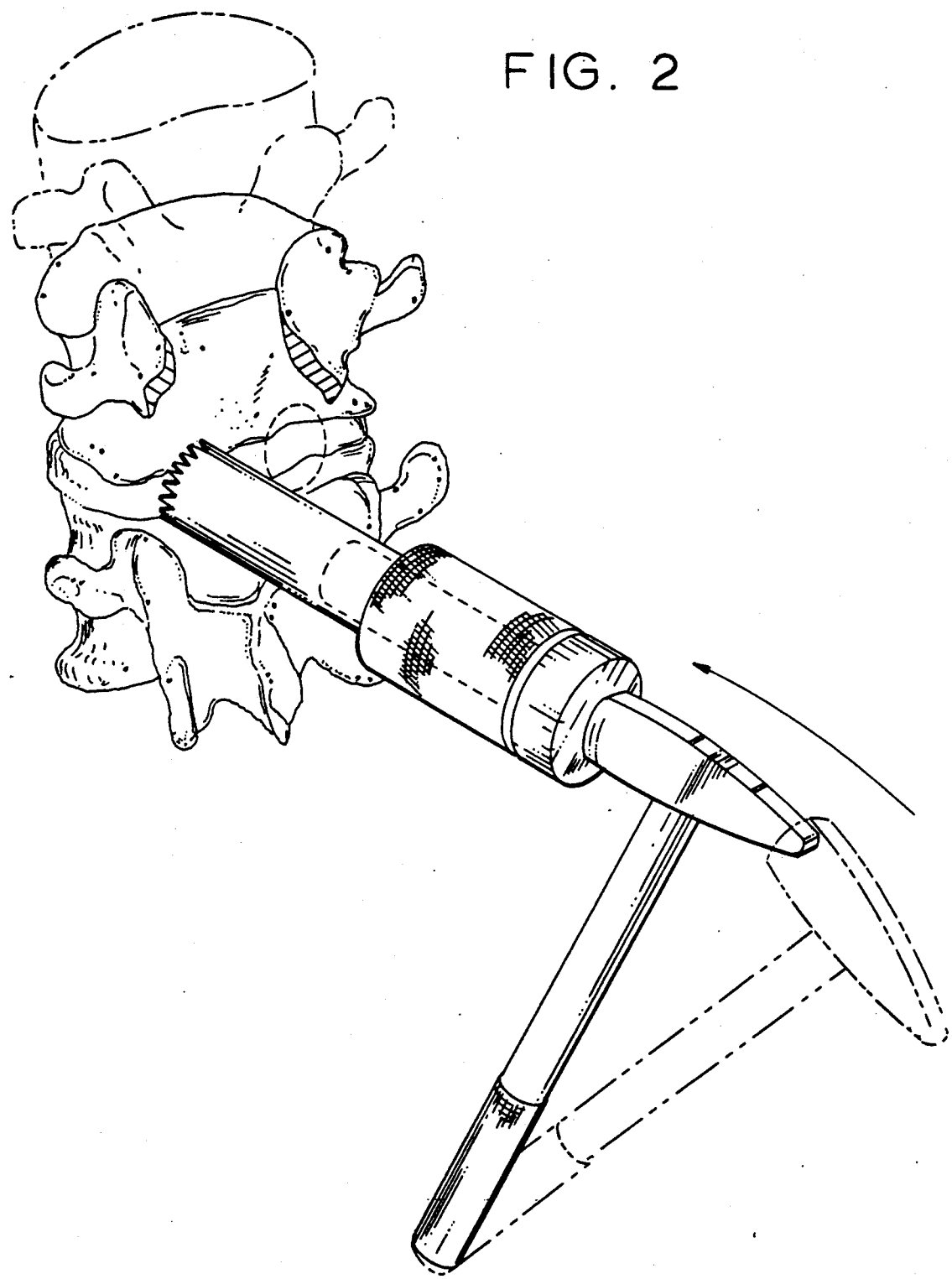
FIG. 2 is a perspective view of the outer sheath being inserted into the vertebra structure.

Referring to FIG. 2 the drill sleeve 10 with the driver 16 installed is shown being driven into two vertebra V on either side of a disc D by hammer H.

Figure 3:
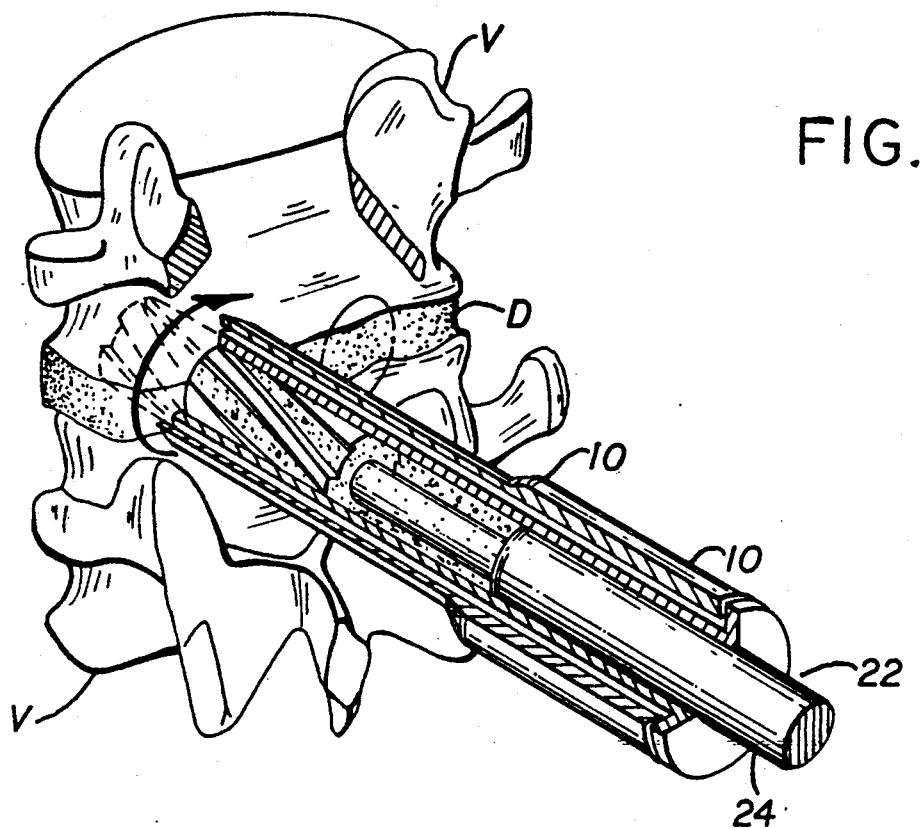
FIG. 3 is a perspective view of the outer sheath and inner sheath assembly, with the drill bit of the present invention.
Figure 3A:
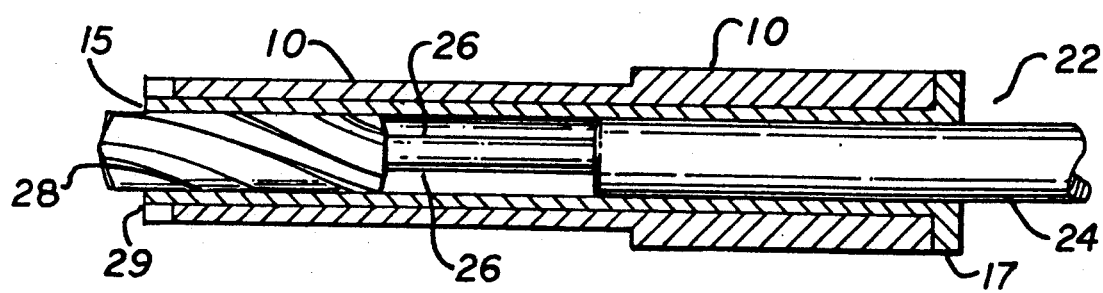
FIG. 3A is a side sectional view of the collar and drill bit of FIG. 3.

Referring to FIG. 3 and 3a the drill assembly is shown. In FIG. 3 the drill sleeve 10 is illustrated in the two vertebra V, straddling the disc D.

The retaining sleeve 15 has an outside diameter slightly smaller than the inside diameter of the drill sleeve 10, and a length substantially the same length as the drill sleeve 10. The retaining sleeve 15 has a collar 17 at its upper end for engaging the top of the drill sleeve 10.

The drill 22 comprises an upper portion 24, a central recessed portion 26 and a lower cutting drill portion 28. The upper 24 and lower portion 28 of the drill 22 have the same outside diameter. The drill 24 has a collar 30 attached to the upper portion 24 of the drill 22.

The outside diameter of the drill 22 is slightly smaller than the inside diameter of the retaining sleeve 15. The length of the drill, from the collar 30 to the end of the drill bit, is such that a predetermined portion of the drill bit 22 extends beyond the end 29 of the sleeve when fully inserted.

Figure 4:
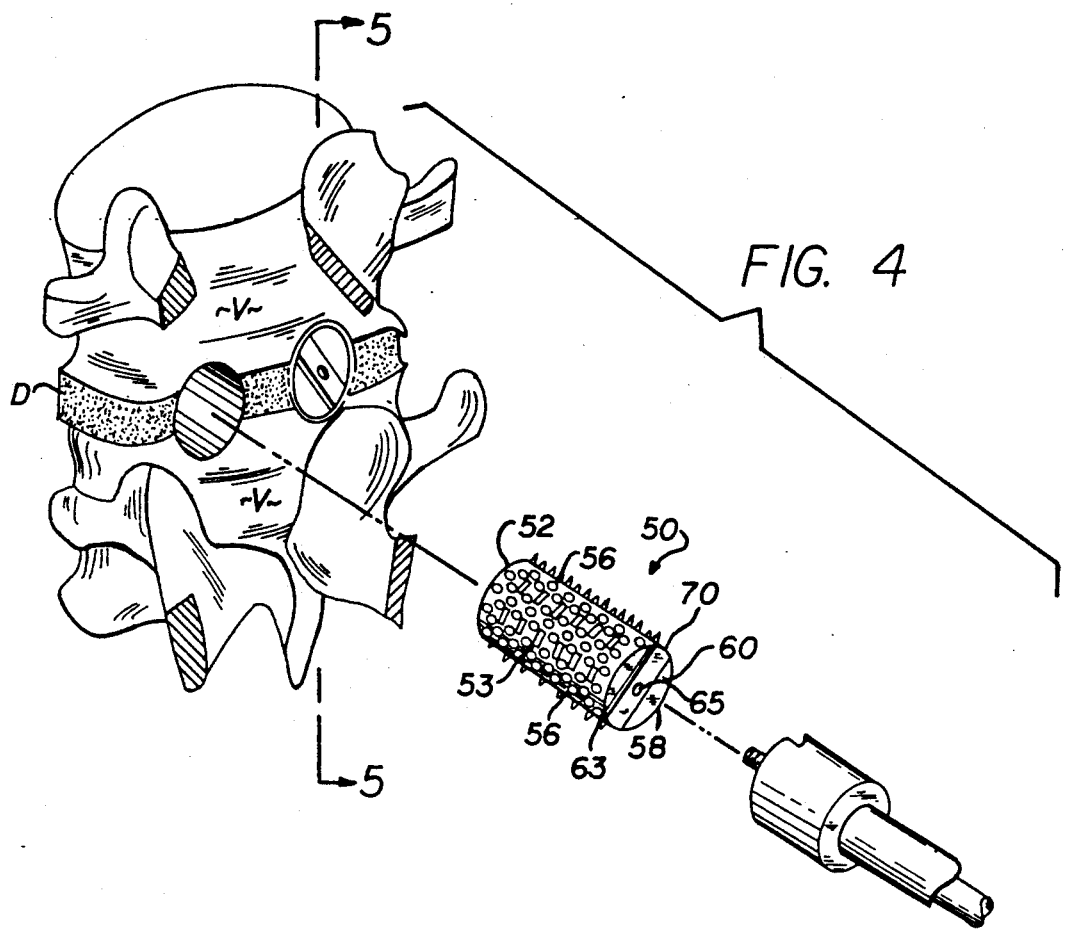
FIG. 4 is a perspective view of a cylindrical implant and vertebra structure.
Figure 4A:
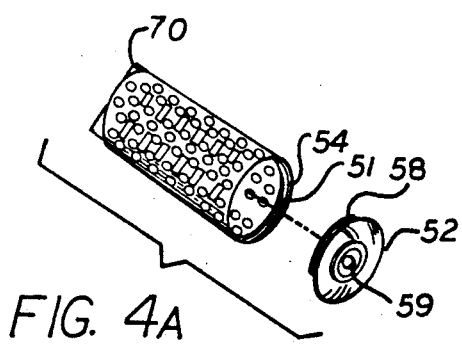
FIG. 4A is a perspective view of one preferred embodiment of the implant.

Referring to FIG. 4, a cylindrical embodiment of the present invention is shown, one implant positioned in the opening in the vertebra and disc formed by the drill 22, and a second implant shown prior to implantation.

The cylindrical implant 50 comprises a hollow tubular member which in the preferred embodiment is made of an ASTM surgically implantable material, and preferably Titanium. The cylindrical implant 50 is closed at on end 52 and open at the other end 54. The outer cylindrical implant 50 has a series of macro-sized openings 56 through the side walls of the cylindrical member 50. A series of external threads 53 are formed on the circumference of the cylindrical implant 50. The threads 53 are locking threads having a series of interjections, the ends of which are blunted and twisted so as to resist unscrewing.

The open end 54 of the cylindrical implant 50 has an internal thread 51 for receiving a complementary cap 52 which has an external thread 58 for engaging the internal threads 51 of the cylindrical member 50. The cap 52 has a hexagonal opening 59 for use with an allen wrench for tightening the cap. A driver engaging element 70 is located on the rear surface 60 of the implant. The driver engaging element 70 comprises a raised rectangular portion 63 and a central threaded opening 65, for engaging the driver apparatus, shown in FIG. 4c and FIG. 4d.

The driving equipment 100 comprises a central tubular rod 102 having a thread fitting into opening 65 in the implant. An enlarged knurled knob 106 is affixed to the other end of the rod 102 for ease in turning. The central rod 102 is enclosed within a hollow tubular member 108, having a narrow lower portion 110 and an increased diameter upper portion 112. At the end of the lower portion 110 is a attachment member 114, having a generally rectangular depression 116 for complementing the driver engaging element 70 of the implant 50. A pair of handles 118 and 120 extend perpendicular from the upper position 112 of the tubular member 108 to assist in turning the driver 100.

The operation is performed in the following manner: (Example Lumbar Spine Posterior Approach) A skin incision is made directly over the interspace to be operated on. The dissection is carried down along side of the superspinous and intraspinous ligaments preserving those structures. A semi hemi laminotomy is performed at the upper level, removing sufficient bone to allow access into the interspace. The ligament flavum is removed and then the dural sac is protected by retracting it medially along with the traversing (inferior) nerve root. The superior nerve root or the root exiting beneath the pedicle at the level above is visualized and protected.

At this time the drill sleeve 10 is placed into the spinal canal with both nerve roots directly inspected and protected. The drill sleeve 10 is imbedded by teeth 12 spanning the disc space from the midline over and it is seated into the two vertebra V across the disc D space by using a driver 20. Once this is done, the driver 20 is removed and a retaining sleeve 15 is placed through the drill sleeve 10. Once seated, sleeve 10 provides absolute protection to the dural sac and nerve roots as the remaining surgery is performed entirely through this sleeve.

The inner sleeve allows for the difference between the outside diameter of the drill 22 and the outside diameter of the threads 53 of the cylindrical implant 50. This then makes it possible to perform the entire operation through the Lummen of the imbedded outer sleeve despite the differences in diameter between the drill and the implant.

A drill 22 is then placed in the retaining sleeve 17. The drill 22 is of such a length that it can not penetrate more then 28 millimeters beyond the end of the drill sleeve 10. This, of course, could be varied and made smaller for enhanced safety. However at the present time 27 to 28 millimeters seems to be safe for probably 3 standard deviations of the population. The drill 22 is attached to a power unit and the drilling takes place.

The recessed central area between the reduced portion 26 allows for the accumulation of the debris generated by the drilling. At this time, leaving the outer sleeve firmly embedded, the retaining sleeve 17 is removed with the drill 22 as a single unit. All the vertebra and disc debris that was generated during the drilling is contained within the recess and against the inside wall of the retaining sleeve 17 and can not come out within the spinal canal. Once the retaining sleeve 17 and drill 22 is out of the patient's operative field, all of the material so generated can be removed.

The next step is that a screw tap is put down through the drill sleeve 10. The tap also has a collar on it that will automatically stop the tap from extending beyond 28 millimeters of penetration. The tap itself has a blunt nose that would also avoid any perforation. The tap is then removed. The tap size has deliberately been selected so that it's inner root diameter is 1.3 millimeters greater than the outside diameter of the drill 22. This insures that the interspace will be distracted by at least that much once the implant is placed. The tap has its outside diameter 1.2 millimeters greater than its root diameter. The tap is removed and the space is now prepared to accept the cylindrical implant 50.

The Implant 50 is prepared by utilizing the trephine, a hollow drill, to obtain a core of pure cancellous bone from the patients iliac crest of slightly smaller diameter than the internal diameter of the implant but approximately 6 mm longer. The implant 50 is placed in a press like device like an ammo loader and the bone graft measuring approximately 32 millimeters is then compressed into the hollow body of the implant (26 mm) so that the bone graft fills the opening 54 and extends through the openings 56. The cap 60 is then screwed on to the implant 50 by use of an allen driver/wrench and the device is ready for implantation.

The inserter/remover is such that it lock onto the implant, so that the implant can be moved either clockwise or counter-clockwise, screwed or unscrewed. The implant itself has for its root diameter the same exact root diameter as the tap which as already noted is already 1.3 millimeters greater than the drill and has an outside diameter, 1.5 millimeters greater than its root. This is also 0.3 millimeters greater than the threads cut by the tap so that in inserting the device it is actually cutting through previously uncut bone helping to insure that it locks in firmly. The threads on the implant 50 are locking threads so that it is easier to screw the device in than for it to be unscrewed. However, with sufficient torque it is possible to extract the device if ones so desires.

Once the implant has been seated it is able to be inserted only 28 millimeters. Since the implant 50 is only 26 millimeters in length, this virtually guarantees that the implant 50 will be recessed into the vertebral bodies more than 2 millimeters and can not protrude into the spinal canal.

Figure 4B:
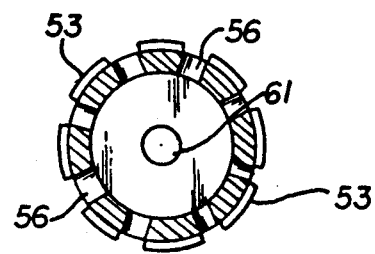
FIG. 4B is a cross sectional view of the implant of FIG. 4A.
Figure 4C:
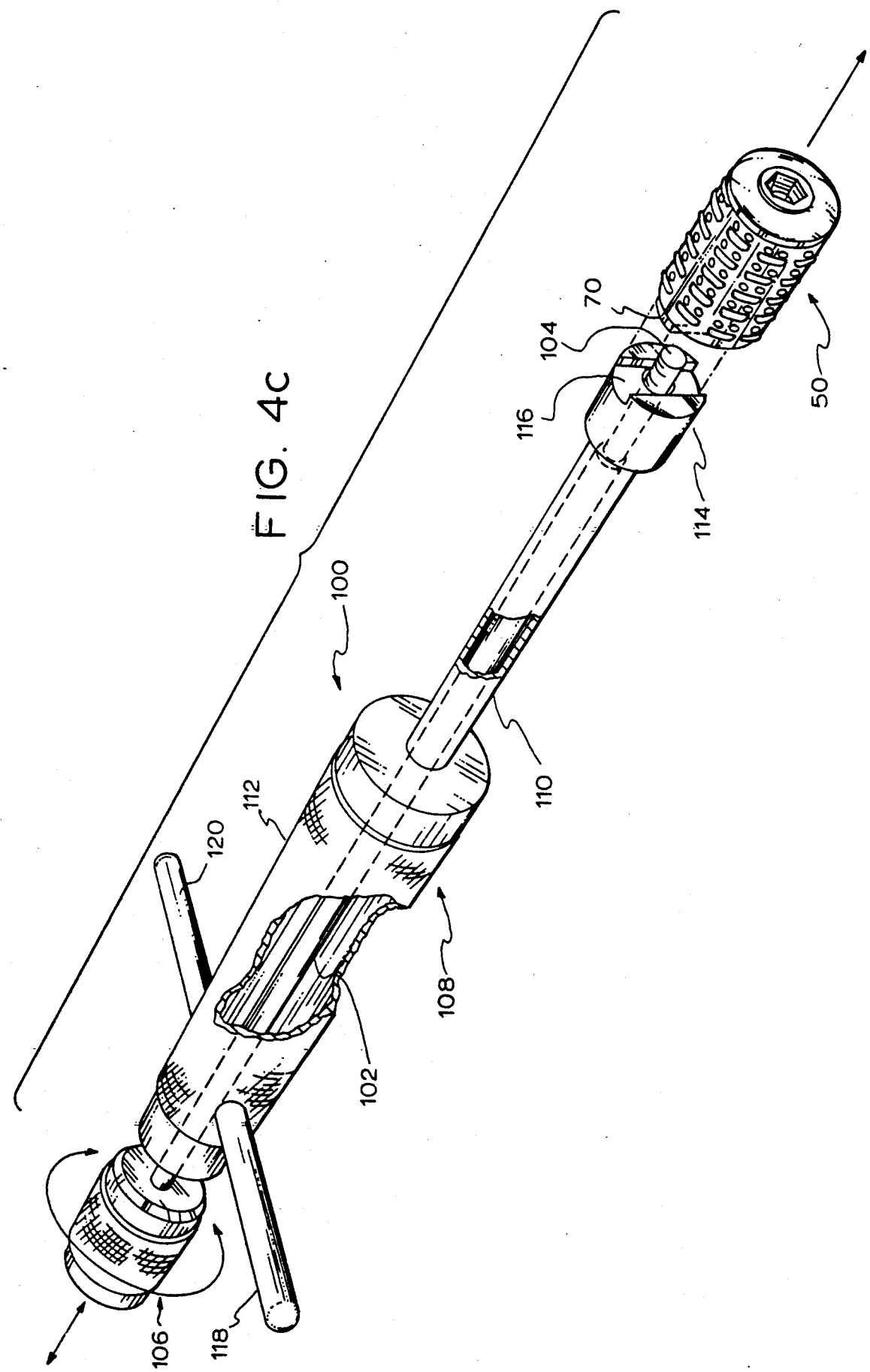
FIG. 4C is the driving and insertion equipment for the implant of FIG. 4A.
Figure 4D:
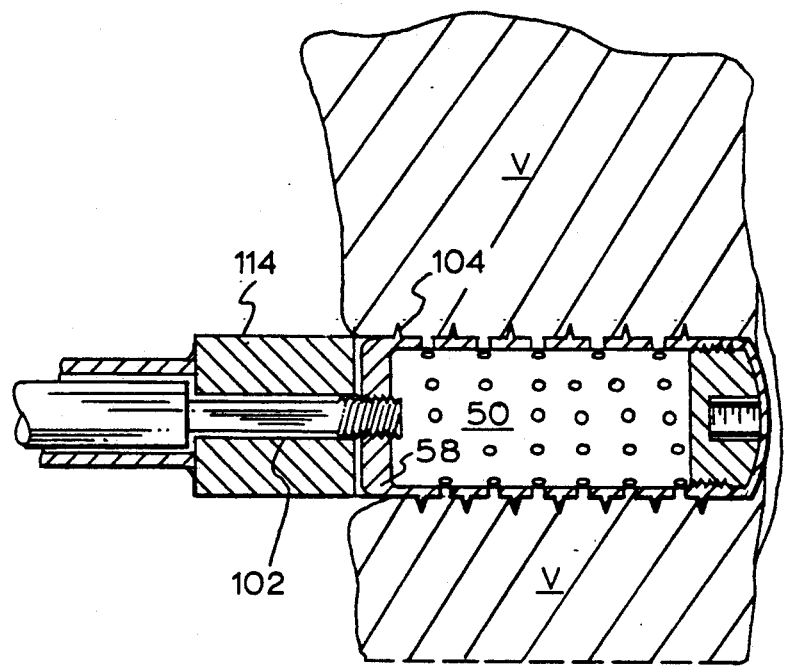
FIG. 4d is a side sectional view of the driver and implant between vertebra.
Figure 5:
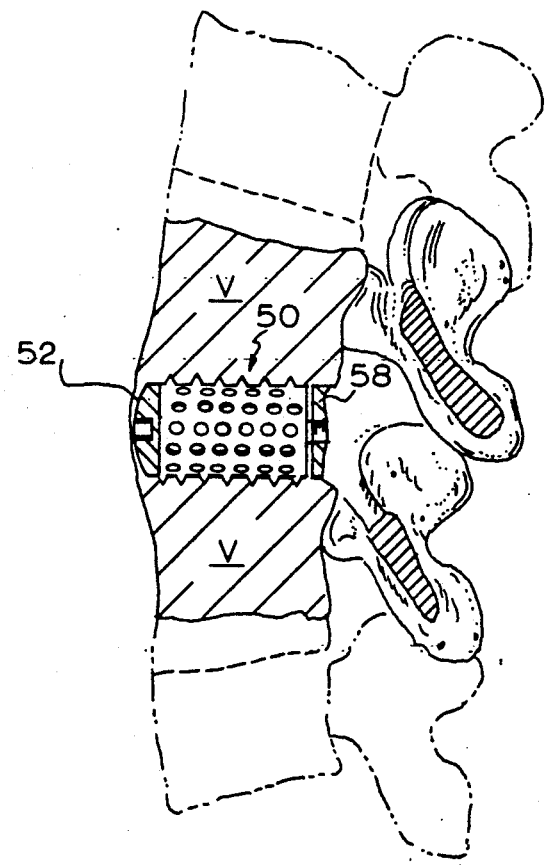
FIG. 5 is a sectional view of the vertebra structure, taken along lines 5—5 of FIG. 4.

Similarly, the implants shown in FIG. 4b can be implanted. The implant in FIG. 4b is a modified solid, having extensive channelling throughout, and has no cap. A central opening 61 permits insertion of the bone graft material into the interior of the implant.

These implants have a surface configuration such as to induce bone ingrowth through the implant, and into the wall of the vertebra in effect inducing fusion from one vertebra in joint to the other, thereby eventually making the implant itself superfluous as the bone would do the work.

The implant itself, because of its being made of stronger material than bone, would provide structural support to the two vertebra while awaiting bone ingrowth. Once the bone ingrowth occurred, however, the implant would be firmly and permanently fixed in place.

As shown in FIG. 4, more than one implant is inserted into the disc space, thereby preventing the rocking motion that would result in the difficulties referred to above in the discussion of the Bagby patent.

While the invention has been described with regards to the preferred embodiment, it is recognized that alternative embodiment may be devised which would not depart from the present invention.

What I claim is:

1. A fusion implant comprising a cylindrical member having an outside diameter larger than the space between two adjacent vertebrae to be fused and a series of threads on the exterior of the cylindrical member for engaging said vertebrae to maintain said implant in place, a plurality of openings in the cylindrical surface of said member, said outside diameter of said cylindrical member being substantially uniform over the entire length of the implant.

2. The implant of claim 1 in which the implant is made from a material designed to promote bone ingrowth.

3. The implant of claim 1 in which said implant has a hollow portion for receiving autogenous bone for promoting bone ingrowth.

4. The implant of claim 3 in which said implant has a removable cap for covering said hollow portion.

5. The implant of claim 4 in which said cap has a thread for screwing onto said hollow portion.

6. The implant of claim 1 in which said implant has means for engaging a insertion/removal device for inserting and removing said insert.

7. The implant of claim 6 in which said engaging means comprises a shoulder and threaded opening.

8. The implant of claim 1 in which said threads are locking threads.

9. The implant of claim 1 in which said threads are interrupted.

* * * * *

UNITED STATES PATENT AND TRADEMARK OFFICE

CERTIFICATE EXTENDING PATENT TERM
UNDER 35 U.S.C. § 156

PATENT NO.      :   5,015,247

ISSUED          :   May 14, 1991

INVENTOR(S)     :   Gary K. Michelson

PATENT OWNER    :   Karlin Technology Inc.

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of 829 days from June 13, 2008, the original expiration date of the patent, subject to the provisions of 35 U.S.C. § 41(b), with all rights pertaining thereto as provided by 35 U.S.C. § 156(b).

I have caused the seal of the Patent and Trademark Office to be affixed this 27th day of August 1998.

Bruce A. Lehman
Assistant Secretary of Commerce and
Commissioner of Patents and Trademarks